United States Patent [19]

Bogie et al.

[11] 3,997,459
[45] Dec. 14, 1976

[54] DENTURE CLEANING COMPOSITION

[75] Inventors: Kenneth David Bogie, Hessle; Noel John Pinto, Hornsea; Peter Norman Ring, Cottingham, all of England

[73] Assignee: Reckitt & Colman Products Limited, London, England

[22] Filed: Oct. 28, 1975

[21] Appl. No.: 626,044

[30] Foreign Application Priority Data

Nov. 8, 1974 United Kingdom ............ 48498/74

[52] U.S. Cl. ..................... 252/99; 134/3; 134/27; 252/100; 252/142; 252/174; 252/DIG. 2

[51] Int. Cl.² ...................... C11D 7/54; C11D 7/08

[58] Field of Search ........... 252/99, 100, 142, 174, 252/134, DIG. 2; 134/3, 27

[56] References Cited

UNITED STATES PATENTS

| | | |
|---|---|---|
| 3,042,621 | 7/1962 | Kirschenbauer ................... 252/99 |
| 3,268,455 | 8/1966 | Bryce et al. ...................... 252/142 |
| 3,607,759 | 9/1971 | Barth ............................... 252/99 X |
| 3,703,470 | 11/1972 | Brennan ........................... 252/99 |
| 3,821,117 | 6/1974 | Breece et al. ..................... 252/99 |
| 3,908,045 | 9/1975 | Alterman et al. ................. 427/213 |

FOREIGN PATENTS OR APPLICATIONS 2,180,864   11/1973   France

*Primary Examiner*—Harris A. Pittick
*Attorney, Agent, or Firm*—Bacon & Thomas

[57] ABSTRACT

A denture cleaning composition comprises an acidic component which gives an acidic solution when the composition is mixed with water and a neutralizing component having a protective coating which causes the neutralizing component to be released over an interval of time to neutralize the acidic solution. A bleaching agent may also be included.

11 Claims, No Drawings

DENTURE CLEANING COMPOSITION

BACKGROUND OF THE INVENTION

This invention relates to cleaning compositions and particularly to compositions for cleaning dentures.

Known compositions for cleaning dentures are generally of two types:
a. alkaline compositions containing an oxidising agent which is effective in bleaching the stains and film which form on dentures but which do not readily dissolve tartar deposits;
b. acidic compositions which are effective in removing tartar deposits but which tend to leave an acidic after taste on the dentures and may cause corrosion in exposed metallic parts.

SUMMARY OF THE INVENTION

According to the present invention there is provided a cleaning composition for dentures comprising an acidic component which provides an acidic solution when the composition is mixed with water and a neutralising component having a protective coating such that, when the composition is mixed with water the protective coating is so affected that the neutralising component is released over a period of time to neutralise the acidic solution.

DESCRIPTION OF PREFERRED COMPOSITIONS OF THE INVENTION

When the cleaning composition is mixed with water an acidic solution is formed. The dentures to be cleaned are placed in this solution. Over a period of time, the neutralising component is released to reduce the acidity of the solution. Because the neutralising component is released over a period of time, the solution remains sufficiently acidic to be capable of removing tartar and film from dentures for the desired time interval. When the neutralising component has been fully released the user can remove the dentures without contacting an acidic solution.

Preferably the acidic solution formed when the cleaning composition is mixed with water has a pH of less than 2.5 preferably less than 2 and the solution remaining when all the neutralising component has been released has a pH greater than 5.5.

The composition may also contain a bleaching agent which may be an oxygenating bleach such as salts of the acid $H_2SO_5$ and industrial forms thereof, such as Oxone (Trade Mark of Du Pont Company), whose active constituent is potassium monopersulphate perborate salts or percarbonate salts.

Suitable acidic components include acids such as sulphamic acid, acetodiphosphonic acid, solid organic acids such as citric acid and tartaric acid or acid salts such as sodium bisulphate.

Preferably, the neutralising component contains a carbonate salt such as sodium carbonate or a bicarbonate salt such as sodium bicarbonate or a mixture thereof so that turbulence is caused by the evolution of carbon dioxide gas which occurs during the neutralisation of the acidic solution formed when the composition has been added to water. Additionally, a phosphate salt such as trisodium phosphate or a hydroxide such as calcium hydroxide may be included in the neutralising component.

The thickness and nature of the protective coating applied to the solid neutralising component will determine the time interval which elapses before the neutralising component is fully released to neutralise the acidic solution.

In any particular composition the time interval may be varied by varying the thickness of the coating applied to the neutralising component. Different coating materials will give different time intervals for similar coating thicknesses.

Suitable coating materials for the neutralising component include, for example, homopolymers or copolymers of ethylenically unsaturated monomers such as acrylic acid and its esters, methacrylic acid and its esters, crotonic acid and esters, ethylene, styrene, esters of vinyl alcohol, vinyl ethers, maleic acid and its esters, allyl alcohol and vinyl pyrrolidones. Examples of suitable copolymers are styrene/acrylic ester copolymers, styrene/allyl alcohol copolymers, vinyl acetate/versatic ester copolymers (versatic acid is a synthetic saturated tertiary monocarboxylic acid having $C_9$, $C_{10}$, $C_{11}$ chain length — The Condensed Chemical Dictionary published by Von Nostrand Reinhold) and carboxylated styrene/acrylic copolymers. Other coating materials which may be used include polycondensates such as alkyd resins, phenolic resins, natural resins such as starch or cellulose and their derivatives.

The coating material may contain plasticisers such as dibutyl phthalate or methyl dioxitol.

The neutralising component to be coated with the coating material is preferably granular in nature. Suitable granular materials may be produced by spraying a granulating liquid onto a fluidised bed of the material in powder form. The spraying of the granulating liquid is stopped when granules of the required size distribution have formed. If very fine powders (diameter $<50\mu m$) are to be fluidised it is advisable to add up to 30% by weight of a material having a larger diameter than the fine powder to the bed. This larger diameter material may be previously-granulated material. The granulating liquid may comprise a solution of a binding agent such as starch in water, polyvinyl pyrrolidone or polyglycols. Solutions or suspensions of the coating materials themselves may, in most cases, also be used for granulating. The granulating liquid may contain dyes, perfumes and/or flavourings.

The coating material may be applied to the neutralising component by spraying an emulsion or solution of the coating material onto the granular neutralising component in a fluidised processor. In such a processor the granular neutralising component is fluidised by passing air into the base of the processor to suspend the granular material in the air stream. If desired the air passed into the processor may be heated to dry the granules before the coating material is applied. The progress of the drying may be monitored by observing the temperature and/or humidity of the incoming air, the temperature of the bed and the moisture content of the outgoing air.

A solution of dye, perfume or flavouring may be sprayed onto the fluidised granular material before the coating material is applied in which case the release of the dye, perfume or flavouring will be delayed.

The emulsion or solution of the coating may be sprayed onto the fluidised granular material through at least one spray nozzle located above the fluidised material. To ensure that the coating material is applied to the granular material as evenly as possible the pressure of the fluidising air should remain constant during the spray coating. It is also important that the temperature of the bed is controlled during the spray coating. The correct choice of spray pattern and droplet size distribution of the sprayed emulsion or solution and of the depth to which the spray penetrates the bed also determines whether the granular material is evenly coated.

The emulsion or solution of the coating material may be sprayed until a predetermined weight of the coating material has been added to the fluidised bed. In the Examples in this specification the weight of coating material added is expressed as a percentage of the weight of the substrate present before the coating material is applied. For example, if the weight of solid material in the emulsion or solution sprayed onto 1000g of neutralising substrate is 200g then this is described as a coated substrate having 20% by weight of coating material applied to it. The weight of coating material added, calculated on this basis, may be up to 100% preferably up to 70% by weight of the neutralising component. If the coating material contains groups, such as carboxylate groups, which are liable to react with the neutralising component, a non-reactive material may be applied to the neutralising component before the protective coating material is applied. For example, when the coating material contains free carboxylate groups which are liable to react with the basic neutralising agent a coating of starch may, advantageously be applied to the neutralising component before the protective coating material is applied. The coating of starch may be applied by spraying a solution of starch in water onto the neutralising material in the fluidised processor.

The emulsion or solution of the coating material may contain colouring agents, perfumes or flavourings which may leach out into the water with which the composition is mixed, before the neutralising component is released or may be released during the neutralisation process.

The coated material may be dried after the coating material has been sprayed onto the neutralising component by heating the fluidising air passing into the processor.

The denture cleaning compositions of the present invention may be used as powders or granules or may be tabletted. Advantageously, powder or granular compositions are packed in sachets containing sufficient of the composition for unit dose application. If the composition is tabletted each tablet may contain sufficient of the composition for unit dose application. Preferably each sachet or tablet contains sufficient of the acidic component to produce a pH of less than 2.5 preferably less than 2 when the contents of the sachet or the tablet are mixed with a predetermined quantity of water. To achieve this the sachet or tablet may contain from 2 to 75% by weight of the acidic component. The sachet or tablet may also contain sufficient neutralising component to give an eventual pH of at least 5.5. Conveniently, the total weight of composition in the sachet or tablet lies in the range 2.5 to 15 grams. The tablets may include one or more tabletting aids for example talc, magnesium stearate, polyglycols, cellulose derivatives, polyvinylpyrrolidone, vinylpyrrolidone/vinylacetate copolymers, Acacia gum or gelatine and may have incorporated therein a material which aids the dissolution of the acidic component. Suitable materials include carbonates, bicarbonates or a mixture thereof present in minor amounts so that the amount of acid is not significantly reduced or a material which does not react with the acid such as starch, polymethylcellulose (Avicel) or other swelling agents.

The composition may contain up to 70% by weight of the bleaching agent.

The cleaning compositions may contain an agent to control foaming when the composition is used and also to minimise redeposition of the tartar removed from the dentures.

A corrosion inhibitor may be incorporated into the compositions to minimise attack by the acidic solution on exposed metallic parts of the dentures being cleaned.

The following Examples illustrate the invention.

All percentages are by weight unless otherwise stated.

EXAMPLE 1

A denture cleaning composition comprising:

| | |
|---|---|
| granular sulphamic acid | 40% |
| a mixture of sodium bicarbonate and sodium carbonate coated with Revacryl 144 | 30% |
| Oxone | 25% |
| Wetting agent (Nansa NSP) | 5% | was prepared by mixing together the solid components. The coated bicarbonate/carbonate mixture was prepared by spraying the solids suspended in a fluidised bed with an aqueous emulsion of Revacryl 144 (a styrene/acrylic ester copolymer manufactured by Harlow Chemicals). Revacryl and Nansa are Trade Marks. The temperature of the fluidised bed was 30° C during the spraying process. The weight of coating applied was 15% by weight of the bicarbonate/carbonate mixture present.

The delayed release of the neutralising component was demonstrated by adding samples (5g) of the above composition to tap water (100 ml) at around 13° C. The tap water had an initial pH in the range 7.2 to 7.5. When the sulphamic acid in the composition had dissolved the pH of the solution was 1.1. After thirty minutes the pH had risen to 2.1 and after 4 hours was 6.5. When the experiment was repeated using tap water at around 40° C the pH rose to 3.9 after 3 minutes and had risen to 5.5 after 20 minutes.

This cleaning composition was useful in cold water as an overnight soaking composition for cleaning dentures. Tartar was removed from dentures during the initial period in which the solution had an acidic pH value. The bleaching agent present removed stains and film from the dentures. The effervescence produced when the carbonate/bicarbonate mixture was released to neutralise the sulphamic acid provided turbulence.

EXAMPLE 2

A denture cleaning composition was prepared as in Example 1 except that the neutralising component was a mixture of sodium carbonate and sodium bicarbonate coated with 5% by weight of a styrene/allyl alcohol copolymer (RJ 100 Monsanto). The coating was applied by spraying a 5% w/w solution of the copolymer in butanol onto the fluidised bicarbonate/carbonate mixture.

A sample (5g) of the composition was added to tap water of pH 7.4 (100 ml) at around 13° C a pH of 1.0 was obtained when the sulphamic acid had dissolved. After ten minutes the pH had risen to 5.0 and after thirty minutes had reached 6.3.

EXAMPLE 3

A denture cleaning composition comprising:

| | |
|---|---|
| granular sulphamic acid | 21.4% |
| Anhydrous trisodium phosphate coated with 15% w/w Emultex 264 | 21.4% |
| Oxone | 17.8% |
| Sodium bicarbonate coated with 20% w/w Emultex 264 | 35.8% |
| Wetting Agent (Nansa SP) | 3.6% | was prepared by mixing the solid components. (Emultex and Nansa are Trade Marks) Emultex 264 is a vinyl acetate/versatic vinyl ester copolymer manufacturered by Harlow Chemicals and was applied by spraying an aqueous emulsion of the copolymer onto the neutralising component in a fluidised processor at 30° C. The coated trisodium phosphate and coated bicarbonate were prepared separately and mixed to give the composition above.

A sample of the composition (14g) was added to tap water (100 ml) having a pH of 7.1 at about 15° C. The pH was then taken at various times and the results are shown below:

| Time (minutes) | pH |
|---|---|
| ¼ | 2.5 |
| 2 | 2.7 |
| 5 | 4.6 |
| 10 | 5.3 |
| 15 | 5.7 |

The mixture of tap water and the composition was not stirred during the period over which the pH measurements were taken. As bicarbonate was released and neutralised the acid carbon dioxide was evolved. The effervescence caused tended to mix the components of the composition and water. When a similar composition containing no coated bicarbonate was used, the coated trisodium phosphate remained at the base of the experimental beaker and no effective neutralisation of the acidic solution was observed.

EXAMPLE 4

A denture cleaning composition comprising:

| | |
|---|---|
| solid acetodiphosphonic acid | 33% |
| sodium bicarbonate coated with 20% w/w Emultex 264 (as in Example 3) | 44% |
| Oxone | 22% |
| Wetting Agent (Nansa SP) | 1% | was prepared by mixing the solid compenents. When a sample (9.1g) of the composition was added to tap water (100 ml) having a pH of 7.2 at around 15° C and the pH taken over a time interval the results shown below were obtained:

| Time (minutes) | pH |
|---|---|
| ¼ | 1.9 |
| 1 | 1.7 |
| 2 | 1.8 |
| 5 | 2.1 |
| 15 | 3.4 |

-continued

| Time (minutes) | pH |
|---|---|
| 25 | 5.5 |

EXAMPLE 5

A denture cleaning composition was prepared comprising:

| | |
|---|---|
| powdered sulphamic acid | 33.3% |
| Oxone | 16.7% |
| coated sodium carbonate | 50.0% |

The coated carbonate was prepared by spraying a 5% aqueous solution of starch onto the fluidised sodium carbonate at 30° C to give 15% by weight of starch added and then spraying an aqueous emulsion of a carboxylated styrene/acrylic copolymer containing methacrylic acid, methyl methacrylate, butyl acrylate and styrene in the ratio 1 : 3.24 : 2.42 : 1.67 onto the fluidised sodium carbonate/starch granules to give 20% added copolymer. The copolymer has free carboxylate groups and the inclusion of starch minimises the possibility of reaction between the acid groups on the polymer and the neutralising substrate.

Tap water (100 ml) at 16° C was added to a sample (12g) of the composition and the pH measured against time. The results shown below were obtained. The tap water had a pH of 7.4 initially.

| Time (minutes) | pH |
|---|---|
| 1 | 1.30 |
| 3 | 1.50 |
| 5 | 1.60 |
| 12 | 2.35 |
| 15 | 2.80 |
| 22 | 5.50 |

EXAMPLE 6

A denture cleaning composition was prepared comprising:

| | |
|---|---|
| powdered sulphamic acid | 25% |
| Oxone | 25% |
| Coated sodium carbonate | 50% |

The coated sodium carbonate was prepared by spraying a 5% aqueous solution of starch onto the granular sodium carbonate in a fluidised processor at 30° C to give 7½% by weight of starch added and then an aqueous emulsion of a carboxylated styrene/acrylic copolymer used in Example 5 was sprayed onto the carbonate/starch granules to give 65% added copolymer.

Tap water (150 ml) at 14° C was added to a sample (12 g) of the composition and the pH measured against time. The results obtained are shown below. The pH of the tap water used was 7.7 initially.

| Time (minutes) | pH |
|---|---|
| 1 | 1.5 |

-continued

| Time (minutes) | pH |
| --- | --- |
| 2 | 1.7 |
| 5 | 2.4 |
| 7 | 5.6 |
| 9 | 6.0 |
| 12 | 6.5 |
| 15 | 7.1 |

EXAMPLE 7

A denture cleaning composition was prepared comprising:

| | |
| --- | --- |
| sulphamic acid | 9.1% |
| Oxone | 63.6% |
| coated sodium carbonate (as in Example 5) | 27.3% |

Tap water (150 ml) at 15° C was added to a sample (5.5g) of the above composition and the pH recorded against time. The results are shown below:

| Time(minutes) | pH |
| --- | --- |
| ¼ | 1.7 |
| 2 | 2.2 |
| 4 | 2.9 |
| 6 | 5.4 |
| 8 | 5.8 |
| 10 | 7.2 |

The cleaning compositions described above have been shown to be more effective at removing tartar and film from dentures than one of the commercially-available alkaline bleaching denture cleaners and because the denture cleaning compositions described in Examples 1 to 7 contain a bleaching agent they also remove stains and film from dentures.

EXAMPLE 8

A denture cleaning composition was prepared comprising

| | |
| --- | --- |
| Powdered sulphamic acid | 46% |
| coated sodium carbonate (as in Exammple 5) | 54% |

Tap water (100 ml) at 18° C was added to a sample (13 g) of the composition and the pH measured against time. The results shown below were obtained.

| Time(minutes) | pH |
| --- | --- |
| 0 | 1.6 |
| 5 | 1.9 |
| 10 | 2.9 |
| 18 | 5.1 |
| 20 | 5.6 |

The tap water initially had a pH of 7.3.

Further samples of the composition were used to remove tartar from dentures and were found to be at least as effective at tartar removal as a commerically available liquid cleaner containing hydrochloric acid. In this comparison test several sets of dentures were cleaned by soaking them in the mixture formed when water is added to a sample(13 g) of the composition of Example 8 for 20 minutes. At the end of this time the mixture in which the dentures had soaked had been neutralised and the dentures could be removed without the user's fingers coming into contact with an acidic solution. Several sets of dentures were also cleaned using a commercially available liquid denture cleaner. The liquid acid cleaner used in this comparison was brushed onto the dentures and then rinsed off as directed by the manufacturers of the product. The cleaned dentures were then examined by an experienced observer who concluded that the composition of Example 8 was at least as good at tartar removal as the liquid acid cleaner.

We claim:

1. A solid denture cleaning composition comprising a tartar dissolving amount of an acidic component which dissolves to provide an acidic solution when the composition is mixed with water and a neutralising component having a protective coating, in an amount such that, when the composition is mixed with water the protective coating is so affected that the neutralising component is released over a period of time to neutralise the initially acid solution to a pH of more than 5.5.

2. A denture cleaning composition as claimed in claim 1 wherein the acidic component is selected from the group consisting of sulphamic acid, acetodiphosphonic acid, citric acid, tartaric acid and sodium bisulphate.

3. A denture cleaning composition as claim in claim 1 wherein the neutralising component is selected from the group consisting of a carbonate salt, a bicarbonate salt, a mixture of carbonate and bicarbonate salt, a mixture of a bicarbonate salt with a phosphate salt.

4. A denture cleaning composition as claimed in claim 1 wherein the protective coating is selected from the group consisting of polymers containing acrylic acid and its esters, methacrylic acid and its esters, crotonic acid and its esters, ethylene, styrene, esters of vinyl alcohol, vinyl ethers, maleic acid and its esters, allyl alcohol and vinyl pyrrolidone.

5. A denture cleaning composition as claimed in claim 4 wherein the protective coating is selected from the group consisting of a styrene/acrylic ester copolymer, a styrene/allyl alcohol copolymer and a vinyl acetate/versatic ester copolymer.

6. A denture cleaning composition as claimed in claim 1 additionally comprising a bleaching agent selected from the group consisting of a salt of the acid $H_2SO_5$, a perborate salt and a percarbonate salt.

7. A denture cleaning composition as claimed in claim 6 wherein the salt of the acid $H_2SO_5$ is potassium monopersulphate.

8. The denture cleaning composition of claim 1 comprising powdered sulphamic acid and sodium carbonate coated with 15% by weight starch and 20% by weight of a copolymer containing methacrylic acid, methyl methacrylate, butyl acrylate and sytrene in the ratio of 1:3.24:2.42:1.67.

9. A solid cleaning composition for dentures comprising
   a. an acidic component selected from the group consisting of sulphamic acid, acetodiphosphonic acid, citric acid, tartaric acid and sodium bisulphate;
   b. a sufficient quantity of an acid-neutralising component to neutralise said acidic component selected from the group consisting of a carbonate salt, a bicarbonate salt, a mixture of a carbonate with a bicarbonate salt, and a mixture of bicarbonate salt with a phosphate salt;

c. a protective coating around the acid neutralising component comprising a polymer selected from the group consisting of a sytrene/acrylic ester copolymer, a styrene/allyl alcohol copolymer and a vinyl acetate/versatic ester copolymer, the composition being such that, when the composition is added to water the acidic component dissolves to give an acidic solution, and the protective coating formed around the acid-neutralising component so retards the release of the acid-neutralising agent that, for a period of time, the solution remains sufficiently acidic to remove tartar deposits.

10. A solid denture cleaning composition as claimed in claim 9 wherein a coating of starch is applied to the neutralising component before the protective coating is applied.

11. A solid denture cleaning composition as claimed in claim 9 additionally comprising a bleaching agent of the active oxygen releasing type selected from the group consisting of a salt of the acid $H_2SO_5$, a perborate salt and a percarbonate salt.

* * * * *